United States Patent [19]

Beaudoin et al.

[11] Patent Number: 5,798,241
[45] Date of Patent: Aug. 25, 1998

[54] ATP-DIPHOSPHOHYDROLASES

[75] Inventors: Adrien R. Beaudoin, Rock Forest; Jean Sevigny, East Angus, both of Canada

[73] Assignee: Universite de Sherbrooke, Sherbrooke, Canada

[21] Appl. No.: 777,859

[22] Filed: Dec. 31, 1996

Related U.S. Application Data

[63] Continuation of Ser. No. 419,204, Apr. 10, 1995, abandoned.

[51] Int. Cl.$^6$ .............................. C12N 11/00; C12N 9/96; C12N 9/14
[52] U.S. Cl. .................... 435/188; 435/174; 435/177; 435/180; 435/195
[58] Field of Search ................................. 435/195, 180, 435/174, 177, 188

[56] References Cited

FOREIGN PATENT DOCUMENTS

WO94/02015  2/1994  WIPO .

OTHER PUBLICATIONS

C. Maliszewski, et al., "The CD39 Lymphoid Cell Activation Antigen", 153 *J. of Immunol.* 3574–3583 (1994).
D. LeBel, et al., "Characterization and Purification of a Calcium–sensitive ATP Diphosphohydrolase from Pig Pancreas", 255 *J. Biol. Chem.* 1227–1233 (1980).
J. Laliberté, et al., "Kinetic Effects of CA$^{+2}$ and Mg$^{+2}$ on ATP Hydrolysis by the Purified ATP Diphosphohydrolase", 257 *J. Biol. Chem.* 3869–3874 (1982).
F. Moodie, et al., "Purification and characterization of bovine spleen ADPase", 202 *Eur. J. Biochem.* 1209–1215 (1991).
Y. Miura, et al., "Purification and Partial Characterization of Adenosine Diphosphatase Activity in Bovine Aorta Microsomes", 46 *Thromb. Res.* 685–695 (1987).
International Search Report for PCT Application No. PCT/CA96/00223, mailed Nov. 27, 1996.
A. Baykov, et al., "A Malachite Green Procedure . . . Alkaline Phosphatase–Based Enzyme Immunoassay", 171 *Anal. Biochem.* 266–270 (1988).
M. Bradford, "A Rapid and Sensitive Method . . . Protein–Dye Binding", 72 *Anal. Biochem.* 248–254 (1976).
Y. Côté, et al., "Identification and localization of ATP–diphosphohydrolase . . . platelet aggregation", 1078 *BBA* 187–191 (1991).
Y. Côté, et al., "Characterization of ATP–diphosphohydrolase . . . platelet activation in vitro", 1139 *BBA* 133–142 (1992).

K. Hirota, et al., "Inhibitory Effect . . . Platelet Aggregation", 45 *Thrombosis Res.* 201–209 (1987).
U. Laemmli, "Cleavage of Structural Proteins . . . Bacteriophage T4", 227 *Nature* 680–685 (1970).
D. LeBel, et al., "Characterization . . . ATP Diphosphohydrolase from Pig Pancreas", 255 *J. Biol. Chem.* 1227–1233 (1980).
A. Patel, et al., "Insoluble matrix–supported apyrase, deoxyribonuclease and cholinesterase", 178 *BBA* 626–629 (1969).
M. Rigbi, et al., "The Saliva of the Medicinal Leech . . . High Molecular Weight Fraction", 87B *Comp. Biochem. Physiol.* 567–573 (1987).
K. Yagi, et al., "Purification of ATP diphosphohydrolase from bovine aorta microsomes", 180 *Eur. J. Biochem.* 509–513 (1989).
K. Yagi, et al., "Purification and Characterization of Adenosine Diphosphatase from Human Umbilical Vessels", 40 *Chem. Pharm. Bull.* 2143–2146 (1992).
Yagi et al. Chem Pharm Bull 40(8) 2145–2146 (1992).
Baykov et al. (1988). Anal. Biochem. 171:266–270.
Bradford, M (1976). Anal. Biochem. 72: 248–254.
Côté et al. (1991). BBA 1078: 187–191.
Côté et al. (1992). BBA 1139: 133–142.
Hirota et al. (1987). Thrombosis Res. 45: 201–209.
Laemmli (1970). Nature 227: 680–685.
Lebel et al. (1980). J. Biol. Chem. 255: 1227–1233.
Patel et al. (1969). BBA 178: 626–629.
Rigbi et al. (1987). Comp.Biochem. Physiol. 87B: 567–573.
Yagi et al. (1989). Eur. J. Bioch. 180: 509–513.

*Primary Examiner*—Herbert J. Lilling
*Attorney, Agent, or Firm*—Quarles & Brady

[57] ABSTRACT

The present invention relates to two ATP diphosphohydrolases ATPDase enzymes isolated from bovine aorta and pig pancreas, which enzymes have a molecular weight for their catalytic unit of about 78 and 54 Kilodaltons, respectively. A novel process for obtaining a highly purified ATPDase is also an object of the present invention. This process has been successfully applied to the purification of both the pancreatic and the aorta enzymes and is deemed to work in the purification of any ATPDase. For both sources of enzymes, the process allows the specific activity of the enzyme to be increased by at least 10,000 fold when compared to the activity retrieved in the crude cell homogenates. The novel process involves an ion exchange chromatography step, a separation on an affinity column, followed by an electrophoresis under non-denaturing conditions. The two enzymes purified by this process (aortic and pancreatic) are glycosylated and, when deglycosylated, have molecular weights of about 56 and 35 Kdaltons, respectively.

12 Claims, 4 Drawing Sheets

ATP-DIPHOSPHOHYDROLASES

This is a continuation, of application Ser. No. 08/419,204 filed Apr. 10, 1995 now abandoned.

FIELD OF THE INVENTION

The present invention relates to a process of purification to homogeneity of ATP-diphosphohydrolases involved in numerous nucleotide and nucleoside receptor-mediated physiological functions, namely platelet aggregation, vascular tone, secretory, inflammatory and excretory functions and neurotransmission. These enzymes, which have been particularly obtained from bovine aorta and pig pancreas have been purified and their catalytic unit identified.

BACKGROUND OF THE INVENTION

ATP-diphosphohydrolases (ATPDases) or apyrases (ec 3.6.1.5) have been found in plants, invertebrates and vertebrates. The enzyme catalyses the sequential hydrolysis of the γ- and β-phosphate residues of triphospho- and diphosphonucleosides. These enzymes are generally activated in the presence of divalent cations $Ca^{+2}$ or $Mg^{+2}$ and inhibited by sodium azide. In plants, the enzymes are found in the cytoplasm, in soluble or membrane-associated forms, and are generally more active at acid pH. Their precise function is not known, but there is some evidence that they are involved in the synthesis of carbohydrates. In invertebrates, the enzymes are more active at neutral or alkaline pH. Found mainly in saliva and in salivary glands of hematophagous insects, an antihemostatic role has been demonstrated. In vertebrates, a limited number of studies have already defined a diversity of ATPDases. The catalytic site of these enzymes is generally exposed to extracytoplasmic spaces (ectoenzymes). By their location and kinetic properties, these different types of ATPDases could influence the main systems of the organism, namely vascular and nervous systems. Their specific role in these systems is determined by the presence of purine and pyrimidine receptors which react with triphosphonucleosides and their derivatives at the surface of numerous cell types.

Presence of both ectoATPase and ectoADPase activities in the vascular system has been known for many years, and up until the work of Yagi et al. (1989), they were attributed to two distinct enzymes. The latter purified these activities and showed that in bovine aorta, a single enzyme was responsible for the sequential hydrolysis of ATP and ADP. A mammalian ATPDase had been first described in the pancreas (Lebel et al., 1980) and was further reported in several other tissues. Yagi et al. (1989) proposed that the enzyme from aorta was similar to the previously reported mammalian ATPDase from pancreas and that it was associated with the intima of bovine aorta. Purification to homogeneity was demonstrated by SDS-polyacrylamide gel electrophoresis (PAGE) and silver staining. The apparent molecular weight of the pure enzyme was estimated at 110 KDa. The existence of the ATPDase in the bovine aorta was corroborated by Côté et al. (1991) who, by showing that identical heat and irradiation-inactivation curves with ATP and ADP as substrates, assigned to the same catalytic site the ATPase and ADPase activities. A comparison of the biochemical properties led Côté et al. supra to propose that the bovine aorta enzyme was different from the pancreas ATPDase. Indeed, the enzymes have different native molecular weights, optimum pH and sensitivities to inhibitors. They proposed to identify pancreas enzyme as type I and the aorta enzyme as type II. In the bovine aorta, the enzyme was found to be associated with smooth muscle cells and endothelial cells and could inhibit ADP-induced platelet aggregation. Côté et al. (1991) further showed that concurrent addition of ATPDase and ATP to platelet-rich plasma resulted in an immediate dose-dependent platelet aggregation caused by the accumulation of ADP, followed by a slow desaggregation attributable to its hydrolysis to AMP. In the absence of ATPDase, ATP did not induce any aggregation while ADP initiate an irreversible aggregation which extent is limited by the ADPase activity of the enzyme. ATPDase also attenuated the aggregation elicited by thrombin and collagen but not by PAF (Platelet Activating Factor), the first two agonists having an effect mediated by platelet ADP release. It was therefore suggested that ATPDase had a dual role in regulating platelet activation. By converting ATP released from damaged vessel cells into ADP, the enzyme induced platelet aggregation at the sites of vascular injury. By converting ADP released from aggregated platelets and/or from hemolyzed red blood cells to AMP, the ATPDase could inhibit or reverse platelet activation, and consequently limit the growth of platelet thrombus at the site of injury. In their attempt to further characterize the aorta ATPDase, the present inventors have develop a new process for producing highly purified ATPDases. They have established a procedure by which its specific activity can be increased over and above the activity of a crude cell preparation by more than 10000-fold. They also discovered that the purified enzyme (the catalytic unit) had a molecular weight different from the one previously reported for the native form of the enzyme (190 KD by using the irradiation technique), suggesting that the enzyme may exist in a multimeric form in its native state.

STATEMENT OF THE INVENTION

The present relates to two ATPDases isolated from bovine aorta and pancreas, which enzymes have a molecular weight for their catalytic unit of about 78 and 54 Kilodaltons, respectively. A novel process for obtaining a highly purified ATPDase is also an object of the present invention. This process has been successfully applied to the purification of both the pancreatic and the aorta enzymes and is deemed to work in the purification of any ATPDase. For both sources of enzymes, the process allows the specific activity of the enzyme to be increased by at least 300 fold when compared to the activity retrieved in the microsomial fraction of these cells as previously reported for an aortic and pancreatic proteins of a native molecular weight of about 190 and 130 KDa, respectively.

DESCRIPTION OF THE PRESENT INVENTION

The research team to which the present inventors belong has already characterized the pig pancreatic ATPDase, and the latter reassessed the properties of the bovine aorta enzyme. They confirmed that the aorta ATPDase was different from its pancreatic counterpart. They have found previously (Côté et al., 1992) that the aorta enzyme (isolated from a microsomal fraction of the cells) had a molecular weight of about 190 kDa in its native state. In their work for extensively purify this enzyme, they found that the highly purified enzyme had a molecular weight on SDS-PAGE of about 78 KDa. Yagi et al. (1989) have already shown that an ATPDase purified to homogeneity had a molecular weight of 110 KDa. After purifying the enzyme by the present method, the 110 kDa band was indeed absent from SDS-PAGE. A unique band migrating of an estimated weight of 78 KDa was rather revealed. The confirmation of the identity of the purified enzyme was achieved by binding FSBA, an ATP analog binding the enzyme, to the separated and blotted enzyme. The use of anti-FSBA antibodies revealed the presence of the bound enzyme and this binding was inhibited with ATP and ADP. The same procedure was applied to confirm the identification of the pancreas ATPDase Type I.

The present process allows the purification of ATPDases to a very high level. In the aorta, the purified enzyme has a specific activity which is increased by at least 300 fold compared with the specific activity of microsomal fraction (already enriched by about 30 fold from the crude cell preparation).

The present invention will be described hereinbelow with reference to the following Examples and FIGS. which purpose is to illustrate rather than to limit the scope of the present invention.

EXAMPLE 1

Figure 1:
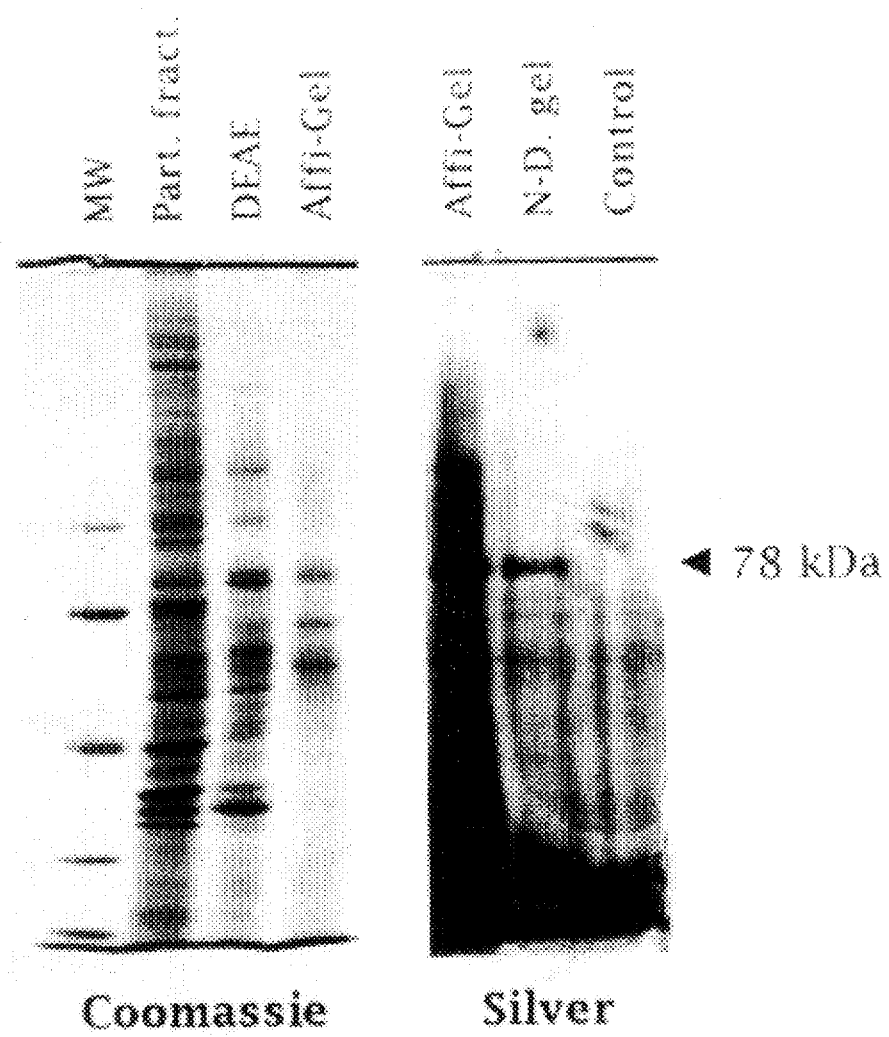
FIG. 1 illustrates the protein composition of the bovine aorta ATPDase (type II) at the different purification steps as determined by SDS-PAGE. Electrophoresis was run in a 7–12.5% polyacrylamide gel. Proteins were stained with Coomassie Blue or silver nitrate dye. MW standards: 97.4, 66.2, 45.0, 31.0, 21.5, 14.4 KDa; particulate fraction (part. fract.), 100 µg; DEAE-agarose fraction, 35 µg; Affi-Gel blue fraction, 20 µg; the lower band of activity was cut out from the non-denaturing gel (N.D. gel); sample buffer alone (Control).

Purification of the ATPDase Type II a) Isolation of the particulate (microsomal) fraction from the bovine aorta:

Bovine aorta, obtained from a local slaughterhouse, were kept on ice and processed within one hour after the death of the animals. All steps were carried out at 4° C. The inner layer was stripped out manually, passed through a meat grinder, and homogenized (10%) with a Polytron™ in the following solution: 95 mM NaCl, Soybean Trypsin Inhibitor (20 µg/mL), 0.1 mM Phenyl-methyl-sulphonyl-fluoride (PMSF) and 45 mM Tris-HCl pH 7.6. After filtering with cheesecloth, the homogenate was centrifuged at 600×g for 15 minutes with a Beckman JA-14 centrifuge at 2100 RPM. The supernatant was recovered and centrifuged at 22,000×g for 90 minutes with the same centrifuge at 12,000 RPM. The resulting pellet was suspended in 0.1 mM PMSF and 1 mM NaHCO$_3$ pH 10.0 with a Potter Elvejehm™ homogenizer at a dilution of 3 to 6 mg of protein per mL. The suspension was loaded on a 40% sucrose cushion and centrifuged at 100,000×g for 140 minutes with a SW 28 Beckman rotor. The enzyme was recovered on the cushion and kept at 4° C. overnight. This membrane preparation was then suspended in 12 volumes of 0.1 mM PMSF and 1 mM NaHCO$_3$ pH 10.0 and centrifuged at 240,000×g for 45 minutes in a SW 50.2 Beckman rotor. The pellet was rinsed twice: once with 0.1 mM PMSF and 30 mM Tris-HCl ph 8.0 and once with 2 mM EDTA and 30 mM Tris-HCl pH 8.0. The final pellet was suspended in 7.5% glycerin and 5 mM Tris-HCl ph 8.0 at a concentration >1 mg of protein per mL and frozen at -20° C., or directly solubilized. At this stage, the specific activity of the ATPDase was enriched by about 33 fold.

b) Solubilization and column chromatoaraphies:

The particulate fraction (pf) was solubilized with 0.3% Triton X-100™ and 30 mM Tris-HCl pH 8.0 at a concentration of 1 mg/mL protein and centrifuged at 100,000×g for 1 hour in a SW 50.2 Beckman rotor. All further steps involving a detergent are practiced with Triton X-100, but any similar detergent (a non-ionic detergent) may be used for achieving the purpose of this invention. The supernatant was loaded on an ion exchange column, preferably containing diethylaminoethyl (DEAE), like DEAE-Bio Gel A Agarose™, preequilibrated with 0.1% Triton X-100™, 7.5% glycerin and 10 mM Tris-HCl pH 8.0. The protein was eluted in the same buffer by a NaCl gradient (0.03 to 0.12M), followed by a 0.1% Triton X-100™ and 2M NaCl wash. Active fractions were pooled in 0.1X buffer E (5X buffer E: 0.5% Triton X-100™, 960 mM glycine, 125 mM Tris-HCl pH 7.0) and electrodialysed in 15 mL cuvettes by an ISCO™ electro-eluter according to the following technique: 1X buffer E was loaded in the apparatus and a 15 mA current was applied per cuvette. The 1X buffer E was changed 4 times at 50 minute intervals. The dialysate was equilibrated at pH 5.9 with 200 mM histidine adjusted to pH 4.0 with HCl (about 20 mM final) and loaded on an Affi-Gel™ blue column preequilibrated with 0.07k Triton X-100™, 7.5% glycerin, 30 mM histidine and 30 mM Tris-HCl pH 5.9. Proteins were eluted by a linear gradient from 100% buffer A to 100% buffer B (buffer A (80 ml): 0.07% Triton X-100™, 7.5% glycerin and 10 mM Tris-HCl pH 6.5; buffer B (80 ml): 1M NaCl, 0.07% Triton X-100™, 7.5% glycerin and 10 mM Tris-HCl pH 7.5), followed by a 1M NaCl, 0.1% Triton X-100™, 100 mM Tris-HCl pH 8.5 wash. The active fraction was dialysed against 0.05% Triton X-100™, 1 mM Tris-HCl pH 8.0, concentrated on a 1 ml DEAE-agarose column as described above, eluted in 0.4M NaCl, 0.07% Triton X-100™, 10 mM Tris-HCl pH 8.0 and dialysed against distilled water.

c) Separation by polyacrylamide gel electrophoresis (PAGE) under non-denaturing conditions:

This type of gel allows for separating proteins upon their molecular weight and electrical charge while preserving their activity in such a way that this activity can be measured after migration. Two polyacrylamide preparations were poured between two glass plates to form a gradient and polymerized. The 4% acrylamide solution was composed of: 4.5 mL of separating buffer (Tris 1.5M pH 8.8+0.4% Triton X-100™), 2.5 mL acrylamide 30%, 180 µL Na deoxycholate 10%, water up to 18 mL, 60 µL APS 10% and 7 µL TEMED. The 7.5% acrylamide solution was composed of the same ingredients except for the volume of acrylamide: 4.5 mL. A stacking gel was extemporaneously prepared and poured at the top of the separating gel, the stacking gel was composed of: 2.5 mL of stacking buffer (Tris-base 0.5M pH 6.8), 6.1 mL of water, 1.34 acrylamide 30%, 0.1 mL Na deoxycholate 10%, 0.1 mL Triton X-100™, 50 µL APS 10% and 10 µL TEMED. Wells are formed in this layer during polymerization. Two volumes of the sample obtained after DEAE-agarose or Affigel Blue columns were added to one volume of sample buffer of the following composition to obtain about 100 µg proteins: 0.07% (v/v) Triton X-100™, 1.5% (w/v) Na deoxycholate, 10% glycerol, 65 mM Tris-base and 0.005% bromophenol blue. The suspended sample was allowed to stand 10 minutes on ice and centrifuged. The supernatant was loaded on gel. The proteins were migrated at 4° C. at a 20 mAmp power in reservoir buffer (0.1% Triton X-100, 0.1% sodium deoxycholate, 192 mM glycine and 25 mM Tris pH 8.3). For revealing activity in the separated bands, the latter were placed in a dosage buffer (Tris-base 66.7 mM, imidazole 66.7 mM, $CaCl_2$ 10 mM, pH 7.5). After preliminary incubation for 30 minutes at 37° C., the substrate (ADP or ATP) 5 mM was added. After 2 to 10 minute incubation, a white calcium phosphate precipitate significative of ATP diphosphohydrolase activity is formed. Three bands are seen for the aorta enzyme and one for the pancreas (these bands were all revealed on gel by silver overstaining). For further characterization, the most active band was loaded on an SDS-PAGE according to Laemmli (1970) and a single band appeared on the gel after silver nitrate staining, which is indicative of an enzyme purification to homogeneity after the non-denaturing gel. FIG. 1 shows the high sensitivity of detection conferred by the use of silver staining compared to a conventional Coomassie blue staining (see lanes 4 and 5). The active band purified from the gel has a molecular weight of 78 KDa when migrated on SDS-PAGE.

d) ATPDase assays during chromatographic steps:

Enzyme activity was determined at 37° C. in the following incubation medium: 50 mM Tris-imidazole (pH 7.5), 8 mM $CaCl_2$ and 0.2 mM substrate (ATP or ADP). Phosphorus was measured by the malachite green method according to Baykov et al. (1988). One unit of enzyme corresponds to the liberation of 1 µmol of phosphate per minute per mg of protein at 37° C. Proteins were estimated by the technique of Bradford (1976).

The ATPDase activity retrieved in isolated fractions are summarized in the following Table:

TABLE 1

ATPDase purification of the bovine aorta ATPDase type II

| Step | Total protein mg | Total activity units | Specific activity units/mg | Yield % | Purification factor -fold | Hydrolysis rate ATP/ADP |
|---|---|---|---|---|---|---|
| Particulate fraction (pf) | 293 | 263 | 0.9 | — | (33)* | 1.5 |
| pf + Triton X-100 | 293 | 117 | 0.4 | 100 | 1 | 1.4 |
| 100,000 g supernatant of solubilized pf | 186 | 91.2 | 0.5 | 78 | 1.2 | 1.3 |
| DEAE column | 15.1 | 72.2 | 4.8 | 62 | 11.9 | 1.1 |
| Affi-Gel blue column | 2.76 | 57.8 | 21 | 49 | 53 | 1.1 |
| Con A | 0.61 | 33.5 | 55 | 29 | 138 | 1.1 |

Figure 2:
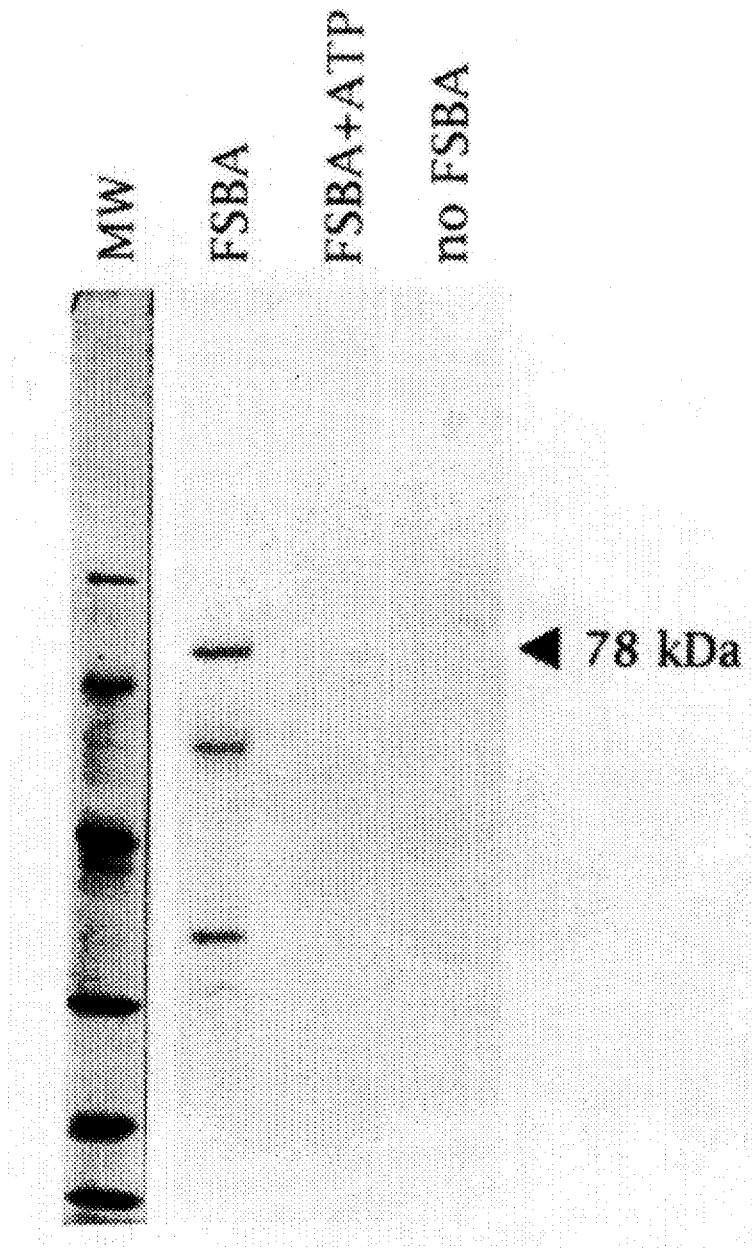
FIG. 2 illustrates a Western blot of FBSA labelled protein (ATPDase type II) isolated from Affi-Gel blue column. Labelled proteins were separated on a 8–13.5% gradient gel by SDS-PAGE, transferred to Immobilon-P membrane, incubated with a rabbit antibody anti-FBSA (1:10,000) and detected by a secondary antibody conjugated to alkaline phosphatase (1:6,000). Twenty µg of protein from Affi-Gel blue column fraction was used for the assays: incubation with FBSA (FBSA); incubation with FBSA with competing Ca-ATP (FBSA+ATP); incubation without FBSA (no FBSA). MW standards are the same as in FIG. 1.
Figure 3:
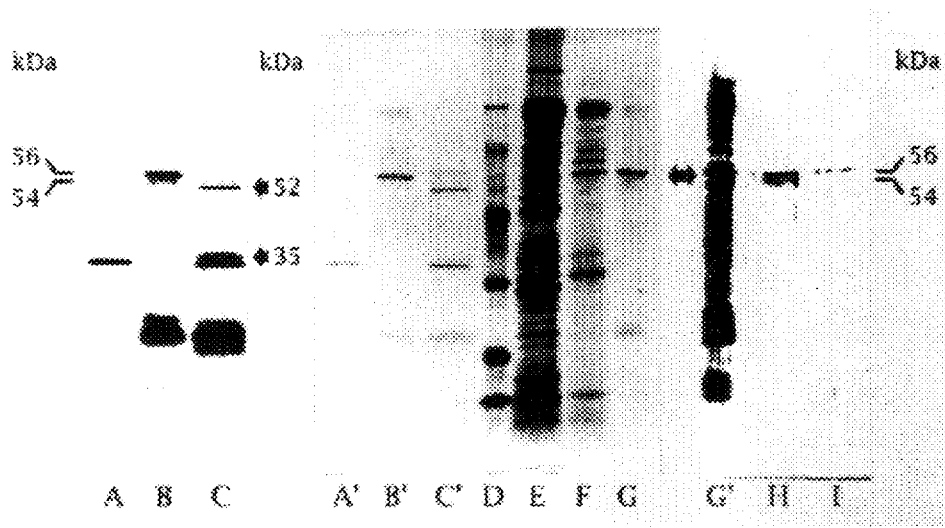
FIG. 3 illustrates the SDS-PAGE protein patterns at the different steps of the purification procedure and after N-glycosidase F digestion of the Affi-Gel blue fraction. Protein samples were fractionated on a 8–13.5% polyacrylamide gradient. A) One unit of N-glycosidase F (silver nitrate stain); B) Six µg from the Affi-Gel blue fraction incubated for 12 h without N-glycosidase F (silver nitrate stain); C) Idem as B with 1 unit of N-glycosidase F (silver nitrate stain); A') Same as A (Coomassie blue stain); B') Same as B (Coomassie blue stain); C') Same as C (Coomassie blue stain); D) MW standards: 97.4, 66.2, 45.0, 31.0, 21.5, 14.4 kDa (Coomassie blue stain), E) ZGM (zymogen granule membrane), 60 µg (Coomassie blue stain); F) Active fraction from DEAE-agarose column, 25 µg (Coomassie blue stain); G) Active fraction from Affi-Gel blue column, 6 µg (Coomassie blue stain); G') Same as G (silver nitrate overstain); H) Activity band located after PAGE under non-denaturing conditions (silver nitrate overstain); I) Control, band located just above the activity band after PAGE under non-denaturing conditions (silver nitrate overstain).
Figure 4:
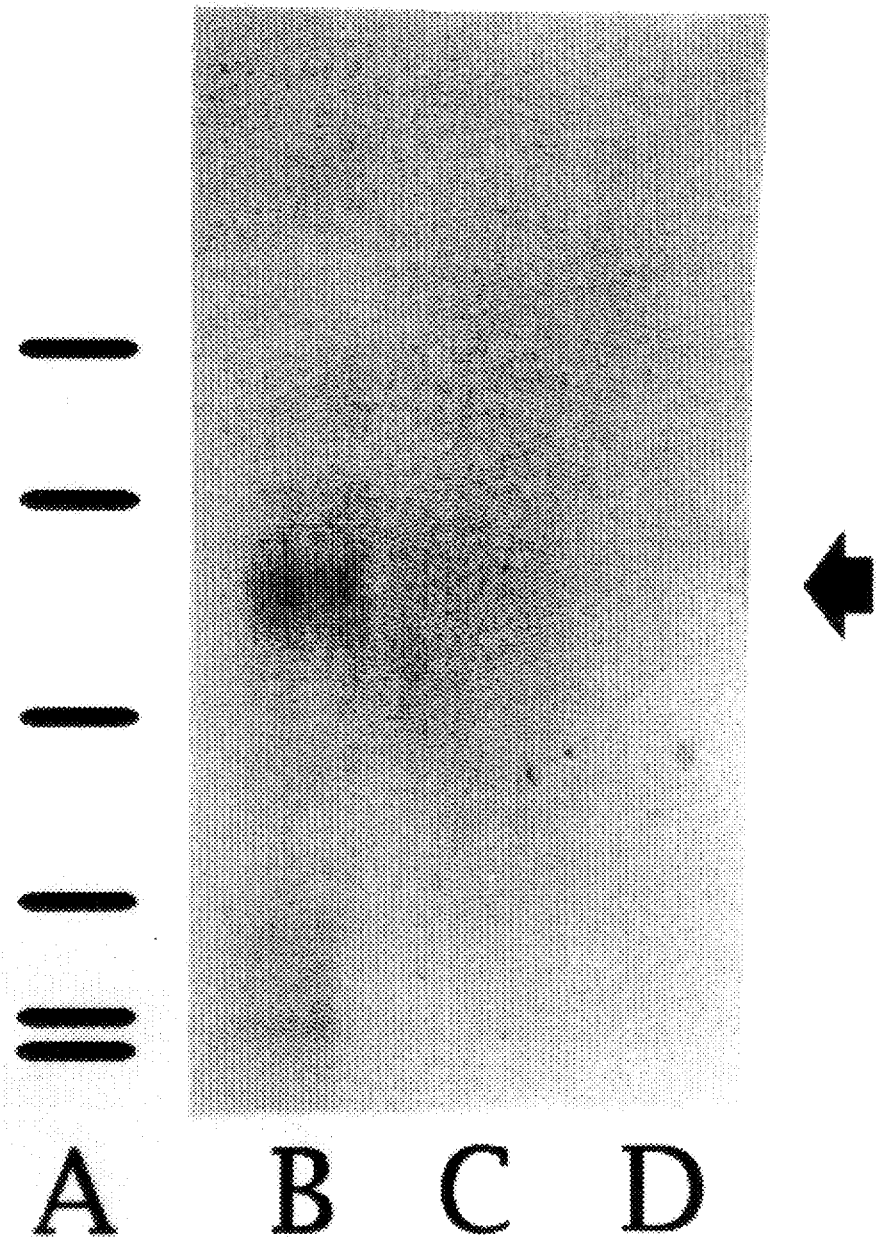
FIG. 4 shows a Western blot of FSBA labelled samples of the pancreatic enzyme type I fraction. Labelled sample were loaded on a 7–12% polyacrylamide SDS-gel, transferred to Immobilon-P membrane, incubated with the rabbit antibody anti-FSBA and detected by a secondary antibody conjugated to alkaline phosphatase. Six µg of Affi-Gel blue column were used in lanes B), C) and D). A) MW standards: 97.4, 66.2, 45.0, 31.0, 21.5, 14.4 kDa; B) FSBA; C) FSBA+competing ADP; D) No labelling.

Details on the purification and condition assays are described in the disclosure. A representative out of five complete purification procedures is shown with ADP as substrate. Determinations were routinely carried out in triplicate. *The starting particulate fraction shows a 33 purification folds as compared to the homogenate (Côte 1991).

e) Confirmation of the identity of ATPDase:

The fraction eluted from Affi-gel was labelled with 5'-p-fluorosulfonylbenzoyl adenosine (FBSA), a marker which forms covalent bonds with adenosine-binding proteins. FSBA blocked the enzyme activity and excess of ATP or of ADP prevents this effect. In addition, FSBA efficiently bound the purified enzyme, as monitored by a Western blot technique using an antibody directed to FSBA, which binding is prevented in the presence of ATP (see FIG. 2) or ADP (data not shown).

The results obtained on SDS-PAGE shows that the enzyme was purified to homogeneity when using the successive steps of solubilization of the particulate fraction, first purification on an ion exchange column, second purification on an affinity column and third purification on non-denaturing electrophoretic conditions. The Affigel Blue column did not achieve purification to homogeneity but allowed a much higher recovery then the 5' AMP-Sepharose™ used by Yagi et al. (about 7 fold higher). Moreover, the use of the Affigel column and the non-denaturing gel allowed us to purify an enzyme that is different from the one disclosed by Yagi.

f) ATPDases are glycosylated proteins:

Purification on Concanavalin A column:

Further purification of the Affi-Gel blue fraction of aorta enzyme was also obtained with Con A agarose column. Briefly, Con A (4 ml beads) and the protein sample from the Affi-Gel blue column were preequilibrated with 0.05% Triton X-100, 100 mM NaCl, 1 mM $CaCl_2$, 1 mM $MnCl_2$ and 20 mM PIPES, pH 6.8, at room temperature. The protein sample was passed through the column at a flow rate of 3 ml/h. 40 ml of the preequilibration buffer was then added to wash the unbound materials at a flow rate of 10 ml/h. The activity was eluted with 20 ml of 0.5M Me-α-D-mannopyranoside diluted in the preequilibration buffer. The purified sample was dialysed and concentrated on a mini-DEAE column as described above.

Precipitation of ATPDase activity with lectin-agarose:

Four lectins conjugated to agarose were tried: Con A, WGA, Soybean agglutinin and UEA. Experiments were carried out at room temperature for Con A, and at 4° C. for the other agglutinins. One hundred μl of each 50% slurry were put in a microcentrifuge tube and washed 4 times with buffer A: 0.0% Triton X-100, 100 mM NaCl and 20 mM PIPES pH 6.8. In the case of Con A, 1 mM CaCl$_2$ and 1 mM MnCl$_2$ were added to this buffer. Twenty μg of ATPDase purified from the Affi-Gel blue column, equilibrated in buffer A, were added to the lectin-agarose beads and rocked for 45 min, then centrifuged for 1 min. The supernatant was kept and the beads were washed 3 times with 1 ml buffer A. Protein bound to the lectins was eluted with 150 μl of 500 mM of the appropriate sugar in buffer A, rocked for 30 min and centrifuged. The elution step was repeated once and the 2 eluates were pooled. The sugar used to eluate proteins from Con A, WGA, Soybean and UEA were Me-α-D-mannopyranoside, D-GlcNAc, D-GalNAc and L-Fuc respectively.

TABLE 2

ATPase binding to lectins

| Lectin-agarose | Fractions | Relative ADPase activity | Presense of the 78 kDa band on SDS-PAGE | Sugar specificity |
|---|---|---|---|---|
| Con A | Supernatant | 5% | traces | Mannose, |
|  | Bound | 95% |  | Glucose |
|  | Eluted | 62% | + |  |
| WGA | Supernatant | 5% | traces | GlcNAc, NeuNAc, |
|  | Bound | 95% |  | Mannose structure § |
|  | Eluted | 69% | + | Sialic acid § |
| Soybean | Supernatant | 100% | + | GalNAc |
|  | Bound | 0% |  |  |
|  | Eluted | 0% | − |  |
| UEA | Supernatant | 100% | + | Fucose |
|  | Bound | 0% |  |  |
|  | Eluted | 0% | − |  |

Twenty μg of ATDPase fraction purified by Affi-Gel blue chromatography were incubated separately with four lectins conjugated to agarose, centrifuged, and the supernatants were collected. Lectins-agarose beads were then washed. Bound proteins were finally eluted with the appropriate sugar as described in the disclosure. This experiment has been done twice in triplicate and the mean is presented. In parallel, the supernatant and the eluted fraction were put on SDS-PAGE, stained with silver nitrate, and looked for the presense of the 78 kDa. The sugar specificity of each agglutinin is also presented.
§ Weak affinities Only WGA bound the ATPDase type II as for Con A. ATPDase binding to these two lectins is indicative of a specificity for the sugars glucose and/or mannose and/or GlcNAc (Glucosamine-N-Acetyl) and/or NeuNAc (Neuraminic-N-Acetyl).

The deglycosylated form had a molecular weight of about 56 KDa, which suggests that about 5 to 11 glycosyl chains are present on the 78 KDa protein (assuming that a glycosyl group may have a molecular weight of 2 to 4 KDa).

EXAMPLE 2

Purification of the ATPDase Type I

The procedure described in Example 1 has been followed for purifying the pancreatic ATPDase type I enzyme, starting from the zymogen granule membrane of pig pancreas.

In deglycosylation experiments, the molecular weight of the catalytic unit has been shown to be shifted from 54 to 35 KDa. Therefore, the chemical procedure exemplified above is deemed to apply to the purification of ATPDases in general.

h) Level of enrichment

The level of enrichment is determined from the data shown in Table 1 for aorta ATPDase type II and from the following Table 3 obtained for pancreatic ATPDase type I.

TABLE 3

ATPDase purification
Results of one out of three preparations is presented. Determinations were carried out in triplicate.

| Steps | Total protein mg | Total activity units | Specific activity (ATP) units/mg | Yield % | Purification factor fold | Hydrolysis rates ATP/ADP |
|---|---|---|---|---|---|---|
| ZGM | 20.0 | 60.8 | 3.0 | — | (160)* | 1.3 |
| ZGM + Triton X-100 | 20.0 | 40.6 | 2.0 | 100 | 1 | 1.3 |
| 100,000 g supernatant of solubilized ZGM | 17.6 | 37.0 | 2.1 | 91 | 1.1 | 1.3 |
| DEAE column | 3.5 | 28.8 | 8.3 | 71 | 4.2 | 1.3 |
| Affi-Gel blue column | 0.31 | 13.8 | 45 | 34 | 23 | 1.3 |

*Laliberté et al. showed a 160 fold purification for the ZGM as compared to the homogenate using ADP as the substrate.

From the crude cell preparation to the Affigel Blue column, the enzymes of both pancreatic and aorta sources were purified to at least a 1600 fold level (see Tables 1 and 3. After the non-denaturing gel, the quantity of proteins falls under the detection level of the method used, which renders difficult the calculation of a specific activity. However, one can roughly estimate the process to reach about a 10 thousand fold purification, as judged by the density of the ATPDase reaction band relative to other proteins on the non-denaturing electrophoretic gel.

Referring to Table 1, the lectin-binding step is not considered properly as an essential step of the purification process. This step has been added to show that the aorta ATPDase is a glycoprotein which, when deglycosylated, shifts from a molecular weight of 78 KDa to a molecular of 56 KDa (representing the proteic backbone). Since the lectin-binding step does not achieve the obtention of a pure protein, the most convenient way to obtain a pure protein is to submit the crude cell preparation sequentially to the ion exchange chromatography, the Affigel Blue chromatography and to non-denaturing gel electrophoresis. The identity of the protein is then confirmed by ATP-labelling with FSBA.

CONCLUSIONS:

Considering that the ATPDase has an antihemostatic role in the saliva of blood-feeding insects and leeches (Rigbi et al., 1987);

Considering that Côté et al. (1992) have demonstrated bovine ATPDase type II has platelet anti-aggregant properties by converting ADP to AMP;

Considering the low Km of the aorta type II enzyme (µM), the optimum pH of catalysis pH 7.5–8.0, its localization at the surface of endothelial and smooth muscle cells of blood vessels (Côté et al., 1992);

Considering that the purified enzyme keeps its original characteristics;

It sounds predictable that the aorta enzyme produced in the present invention can be introduced in the circulatory system of mammalians to reduce platelet aggregation and thrombogenicity.

Furthermore, considering that a crude microsomal bovine ATPDase type II fraction has been successfully conjugated to agarose and that the conjugate could reduce ADP induced platelet aggregation (Hirota et al., 1987);

Considering that a semi-purified plant ATPDase has been successfully coupled to the following matrices: CM-cellulose, copolymers of L-alanine and L-glutamic acid, polyaspartic acid, polygalacturonic acid, Elvacite 2008™ (methyl methacrylate) and ethylene-maleic acid co-polymer (Patel et al., 1969);

We propose that the purified ATPDase type II can be coupled to artificial polymers/biomaterials to reduce thrombogenicity (platelet aggregation).

Therefore, pharmaceutical compositions for use in the reduction of platelet aggregation and thrombogenecity are under the scope of the invention. These compositions should contain, as an active ingredient, the ATPDase type II of this invention combined to an acceptable carrier without excluding any form or formulation of such compositions.

The present invention has been described hereinabove; it will become apparent to the skilled reader that variations could be brought thereto without departing from the teachings of the present disclosure. Such variations are under the scope of this invention.

BIBLIOGRAPHY:
Baykov et al. (1988). Anal. Biochem. 171: 266–270.
Bradford, M (1976). Anal. Biochem. 72: 248–254.
Côté et al. (1991). BBA 1078: 187–191.
Côté et al. (1992). BBA 1139: 133–142.
Hirota et al. (1987). Thrombosis Res. 45: 201–209.
Laemmli (1970). Nature 227: 680–685.
Lebel et al. (1980). J. Biol. Chem. 255: 1227–1233.
Patel et al. (1969). BBA 178: 626–629.
Rigbi et al. (1987). Comp. Biochem. Physiol. 87B; 567–573.
Yagi et al. (1989). Eur. J. Biochem. 180: 509–513.

What is claimed is:

1. A mammalian ATP diphosphohydrolase (ATPDase) isolated and purified from bovine aorta characterized by the following physico-chemical properties:

a catalytic unit having a molecular weight on denaturing polyacrylamide gel electrophoresis of about 78 KDa; and a deglycosylated form of said catalytic unit having a molecular weight on SDS-PAGE of about 56 KDa.

2. A composition for use in the reduction of platelet aggregation and thrombogenicity which comprises as an active ingredient the mammalian ATP diphosphohydrolase of claim 1, together with a pharmaceutically acceptable carrier.

3. An isolated and purified mammalian type II ATP diphosphohydrolase (ATPDase) obtainable from bovine aorta having the following physico-chemical properties:

(a) an estimated molecular weight of about 78 kDa as determined by denaturing polyacrylamide gel electrophoresis;

(b) an estimated molecular weight in its deglycosylated form of about 56 kDa as determined by denaturing polyacrylamide gel electrophoresis;

(c) an optimum pH of catalysis of about pH 7.5 to 8.0;

(d) a Km in the micromolar range;

(e) a localization at the surface of endothelial and smooth muscle cells of blood vessels; and (f) said native form binding 5'-p-fluorosulfonylbenzoyl adenosine (FSBA).

4. The isolated and purified mammalian type II ATPDase of claim 3 having been purified from a crude cell homogenate to a level superior to about 4000-fold as compared to said homogenate.

5. An aggregation and thrombogenicity-reducing composition which comprises as an active ingredient the mammalian ATP diphosphohydrolase of claim 1 together with a pharmaceutically acceptable carrier.

6. An aggregation and thrombogenicity-reducing composition which comprises as an active ingredient the mammalian ATP diphosphohydrolase of claim 3 together with a pharmaceutically acceptable carrier.

7. A composition for sequentially hydrolysing ATP and ADP which comprises as an active ingredient the mammalian ATP diphosphohydrolase of claim 1 together with a pharmaceutically acceptable carrier.

8. A composition for sequentially hydrolysing ATP and ADP which comprises as an active ingredient the mammalian ATP diphosphohydrolase of claim 3 together with a pharmaceutically acceptable carrier.

9. The composition of claim 5, wherein said mammalian ATPDase has been coupled to an artificial polymer and/or biomaterial.

10. The composition of claim 6, wherein said mammalian ATPDase has been coupled to an artificial polymer and/or biomaterial.

11. The composition of claim 5, wherein said mammalian ATPDase has been conjugated to agarose.

12. The composition of claim 6, wherein said mammalian ATPDase has been conjugated to agarose.

* * * * *